United States Patent [19]

Modrovich

[11] 4,394,449

[45] * Jul. 19, 1983

[54] STABILIZATION OF COENZYMES IN AQUEOUS SOLUTION

[76] Inventor: Ivan E. Modrovich, 1043 Mesa Dr., Camarillo, Calif. 93010

[ * ] Notice: The portion of the term of this patent subsequent to Jul. 7, 1998, has been disclaimed.

[21] Appl. No.: 121,225

[22] Filed: Feb. 13, 1980

[51] Int. Cl.³ .......................... C12N 9/96; C12Q 1/58; C12Q 1/50; C12Q 1/34
[52] U.S. Cl. .................................... 435/188; 435/12; 435/17; 435/18; 435/26
[58] Field of Search .................. 435/12, 17, 18, 26, 435/188

[56] References Cited

U.S. PATENT DOCUMENTS

| | | | |
|---|---|---|---|
| 3,413,198 | 11/1968 | Deutsch | 435/17 X |
| 4,189,536 | 2/1980 | Green | 435/12 |
| 4,218,536 | 8/1980 | Maurukas | 435/14 |
| 4,247,633 | 1/1981 | Case et al. | 435/14 X |
| 4,277,562 | 7/1981 | Modrovich | 435/17 |

FOREIGN PATENT DOCUMENTS 7603588  10/1976  Netherlands .

*Primary Examiner*—David M. Naff
*Attorney, Agent, or Firm*—Christie, Parker & Hale

[57] ABSTRACT

A stabilized aqueous coenzyme solution is disclosed for use in the clinical assay of a selected biological constituent through the enzymic reaction of an enzyme with a selective substrate for the enzyme and a coenzyme. The aqueous coenzyme solution comprises at least one first enzyme and a first substrate for selectively reacting with the first enzyme in the assay, a coenzyme for interacting with the first enzyme and first substrate in the assay which coenzyme degrades forming a coenzyme conversion product, and at least one second enzyme and second substrate selective for the second enzyme which react with the coenzyme conversion product to regenerate the coenzyme.

27 Claims, No Drawings

STABILIZATION OF COENZYMES IN AQUEOUS SOLUTION

BACKGROUND OF THE INVENTION

The present invention relates to the stabilization of labile coenzymes in aqueous solutions. In a particular aspect, the present invention relates to stabilized coenzyme solutions for determining urea. Such particular stabilized solutions have utility in determining the quantitative amount of urea in human sera, such as blood, plasma and the like.

Stability of coenzymic solutions used in diagnostic assays in important in providing methods of analysis which exhibit precision and uniformity among separate determinations when conducted over a period of elapsed time. Instability of coenzyme solutions, in addition to not providing reproducibility of assays, can also add to the ever increasing cost of medical services because the unstable coenzyme solutions need to be discarded and fresh solutions formulated.

It has recently been estimated that about 25 percent of all in vitro diagnostic tests conducted annually in the United States are unreliable. Unreliable tests can result in unnecessary medical treatment, the withholding of necessary treatment and lost income. Because of their high specificity, the use of enzyme determinations has significantly increased during the last few years and indications are that this trend will continue. However, rigorous quality control measures are required to assure the accuracy and consistency of results. This requirement derives from the fact that the exact nature of coenzymes, as well as mechanisms of their reactions and coenzymes remains unknown for the most part.

At present, the greatest limitation in the diagnostic reagent manufacture, by far, lies in the unstable characteristics of the enzymic and coenzymic solutions. Current urea diagnostic methodologies require the use of labile ingredients. Due to the labile nature of the coenzymes, rigorous quality control is required over the production of such coenzymic solutions, in the reconstituting dry media preparations and formulation of such coenzymic solutions. Such quality control is costly. Moreover, if such control in any step in the process is not maintained within a high degree of control standards, the quality of the final product can be reduced materially leading to decreased precision in assay results.

The present commercial state-of-the-art used for stabilizing the reactive ability of enzymes or coenzymes is by locking them into a solid matrix, either by freeze drying, dry blending such as used for tableting dry powders primarily in the pharmaceutical, diagnostic and related industries, and immobilization by locking the chemical structure of the enzyme or coenzyme into a solid matrix. Contrary to the sophistication these terms imply, these approaches are neither practical nor desirable and are also expensive. The manufacturer is forced to remove the water and supply a partial product, thus relinquishing part of the quality control cycle in the dilution and use of the final product. Laboratories are forced to pay the high cost of packaging, reagent waste, freeze drying and dry blending. Usefulness of the product is further limited by packaging modes and sizes.

Furthermore, good product uniformity is difficult to achieve, especially in the laboratories where the products are to be utilized in diagnostic assay. Generally, the reconstituted freeze-dried solutions have a relatively short stability such as about 24 hours to 5 days at room temperature conditions. Their use is then limited by such a short shelf-life.

The present invention is uniquely designed so that the coenzymes, although labile in an aqueous liquid matrix, are effectively "stabilized" thereby controlling the activity of the labile ingredients in the liquid solution. The means of stability insures long-term stability in an aqueous liquid media. Moreover, close tolerance control can be achieved in the manufacturing of a high quality product which eliminates the inconvenience of the rigid package size, the high cost of packaging and freeze drying, and reagent waste.

In the clinical diagnostic field the commercial application of coenzymic analysis is represented by, but not limited to, the diagnostic reagents used to determine and quantitate the following constituents in ciological fluids:

1. glutamic-oxalacetic transaminase (SGOT);
2. glutamic-pyruvic transaminase (SGPT);
3. lactic dehydrogenase (LDH);
4. creatine phosphokinase (CPK);
5. α-hydroxybuteric dehydrogenase (α-HBD);
6. glucose (via hexokinase-G-6-PDH or glucose dehydrogenase); and
7. blood urea nitrogen (BUN).
8. triglycerides The reagents for performing the diagnostic analyses for the above constituents react similarly, contain some common labile ingredients, and some of the chemical reactions involved are common. The following Reaction Scheme I is presented as a model to illustrate the general nature of the reactions involved:

REACTION SCHEME I

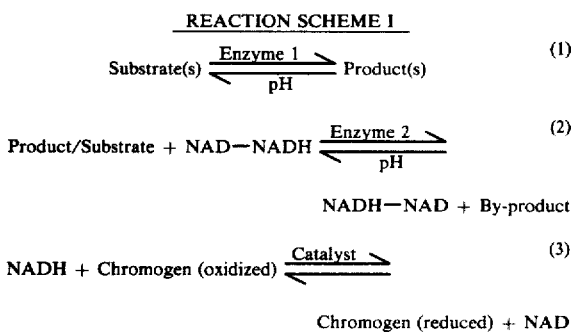

All enzymatic reactions listed above will follow this general scheme, where reaction (2) is usually referred to as the coupling reaction, reactions (2) or (3) are the measuring reactions, and reaction (1) may be characterized as the primary reaction. It is understood, however, that not all three reactions are required for measurement, in fact, they may be limited to two, or one. In the case of the ultraviolet measurement of lactic dehydrogenase (LDH) activity, only reaction (2) is involved, as follows:

REACTION SCHEME II - LDH

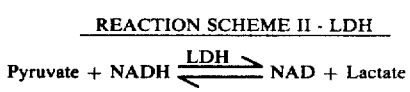

Conversely, more than the three reactions listed can be involved as in the case of creatine phosphokinase (CPK):

REACTION SCHEME III - CPK

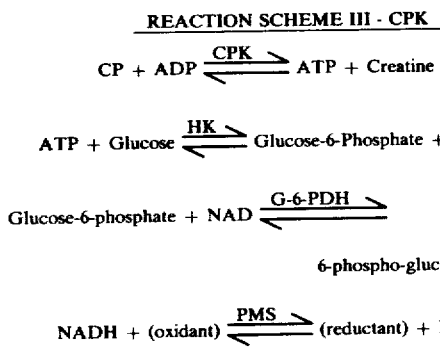

In this case, reactions (2) and (3) may be considered the coupling reactions, reactions (3) or (4) the measuring reactions, and reaction (1) the primary reaction.

The following symbols are used herein and in the above reaction schemes. The symbols used are the generally acceptable symbols for the clinical diagnostic field.

SYMBOLS

CP = Creatine phosphate
ADP = Adenosine-5'-diphosphate
ATP = Adenosine triphosphate
HK = Hexokinase
NAD = nicotinamide-adenine dinucleotide
NADH = nicotinamide-adenine dinucleotide, reduced
G-6-PDH = Glucose-6-phosphate dehydrogenase
INT = tetrazolium salt
PMS = phenazine methosulfate Referring to the Reaction Scheme I, it becomes obvious and is general knowledge that the use of the reaction sequence permits the analytical quantitation of either the reaction substrates/products or the catalyzing enzymes.

The quantitation of these constituents in biological fluids is a well accepted and widely used diagnostic tool in diagnosis and treatment of human and animal disease states.

Enzymes are large molecular weight complex protein molecules, usually of unknown chemical structure. They are presently classified by their catalytic activity and extreme substrate specificity. Enzymes may be redefined as biological catalysts, capable of catalyzing a reaction of a single substrate or a reaction of a similar group of substrates.

Coenzymes are lower molecular weight organic chemicals of well-defined structure, whose reactions or interactions are necessary for specific enzyme assay or reaction. They are catalyzed resulting in an irreversible change in the coenzyme's structure and/or atomic composition. Coenzymes are necessary in enzymic clinical assay procedures and are useful for measurements. Some coenzymes have strong absorbance and their reactions are stoichiometric with the substrate. Therefore, the creation or disappearance of the absorbing form can be followed photometrically. Nicotinamide adenide dinucleotide (NAD) and its reduced form (NADH) are used in many important clinical assays, such as the SGOT, SGPT, BUN, CPK, glucose, HBDH and LDH assays previously described. NAD and NADH have a molecular weight of about 700 and are very complex organic molecules. NADH absorbs strongly at 340 nm whereas NAD does not absorb at this wavelength.

NADH is extremely unstable in water solution or in dry form when exposed to humid environments. Even when frozen, NADH must be kept free of moisture. Stability is better at alkaline pH, whereas at acid pH NADH decomposes very rapidly in a matter of minutes. Neither the exact mechanism, nor the end products are of significance except that decomposed NADH can no longer effectively function as a coenzyme for enzymic reactions requiring NADH, nor does it possess the extinction coefficient at 350 nm. The typical commercial form is a dry desiccated package or a freeze-dried form stored under nitrogen. NADH is classically insoluble in most organic solvents.

With regard to the quantitative measuring of urea, some methods are based on colorimetric and spectrophotometric analyses. For example, in the reaction sequence:

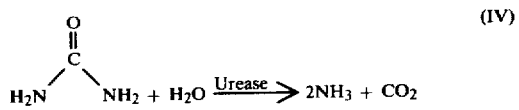

The production of ammonia or $CO_2$ can be quantitatively measure photometrically. The ammonia produced can be measured photometrically by the reaction:

The intensity of the blue color produced can be correlated to the amount of ammonia. The ammonia can also be measured through the following reaction sequence:

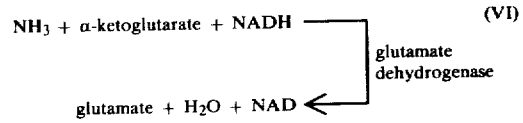

In this reaction sequence the coenzyme NADH acts as a reducing agent. The NADH has an absorbance at 340 nm and the NAD does not. Thus, the absorbance at 340 nm can be correlated to the amount of $NH_3$ present in a sample which in turn can be correlated to the amount of urea.

SUMMARY OF THE INVENTION

Labile coenzymes are treated according to the invention resulting in long term stability without affecting coenzymatic reactivity or photometric absorptivity. The invention provides reagents where quality control is assured throughout manufacturing, packaging, storage and use. The inconvenience of rigid package size is eliminated as is the high cost of packaging, freeze drying and reagent waste. Liquid enzyme and coenzyme systems provide application flexibility. Separation of the ingredients is easily accomplished with negligible manufacturing cost. The liquid enzyme and coenzyme systems herein provide the flexibility of triggering the desired reaction after all side reactions have been dissipated.

The stabilized coenzymes of the invention are assessed in studies which compare the aqueous coenzyme reagents with fresh reagents. The studies show a 1:1 correlation between aged aqueous and fresh reagents with comparable sensitivity and precision. Providing coenzyme reagents in a stable aqueous form enhances the colorimetric applicability of present day NAD/NADH coupled methodologies primarily because the separation of ingredients is easily accomplished. Stable aqueous reagents are especially advantageous where NADH consumption is the basis of measurement and the color reagent must be separated from NADH and the primary reaction. In the ultraviolet mode, the liquid system offers better reagent homogeneity and packaging, as well as flexibility in usage, in contrast to the freeze-dried or dry media preparations.

In diagnostic enzymology, the stabilization of enzyme and coenzyme reagents is a ready-to-use aqueous media is a new and exciting approach to satisfy the needs of the clinical laboratory and the reliability demands of the regulatory authorities. The flexibility of aqueous enzyme and coenzyme systems insures their applicability to automated instrumentation, as well as their convenience in manual testings without reagent waste due to limited shelf life.

Stabilization of labile coenzymes in aqueous solutions is accomplished in accordance with the invention by providing a suitable enzyme and substrate in the solution for regenerating the coenzyme. That is, the coenzyme concentration is maintained in a sufficient diagnostic amount by enzyme regeneration. To enzymically regenerate a coenzyme in a particular analytical, diagnostic, or clinical assay system, enzymes and the substrates with which they react to produce the coenzyme from the coenzyme conversion product produced in the particular assay system and which enzymes are not present within the assay system are selected. Such enzymes and substrates are then added to the assay system in an amount sufficient to provide regeneration of the coenzyme. A particularly preferred enzyme and substrate system for the production of NADH is hexokinase, glucose-6-phosphate dehydrogenase, glucose and ATP. This enzyme and substrate system has utility in regenerating NADH from NAD in the clinical assays of BUN; SGOT; SGPT; HBDH; and LDH. NADH is easily oxidized to NAD through enzymic and/or atmospheric oxidation. Commercial enzyme preparations of LDH and MDH (used in SGOT/SGPT assays), for example, contain other enzymes as impurities capable of oxidizing NADH to NAD thus depleting the available NADH within a few hours at ambient temperatures.

The use of enzymic regeneration of coenzymes in clinical assay systems decreases the need for an initial high coenzyme activity in the assay system. That is, the amount of coenzyme needed in the assay system can be decreased because as the coenzyme degrades, the degradation product of the coenzyme reacts with the added enzymes within the assay system to regenerate some of the coenzyme.

DESCRIPTION OF THE PREFERRED EMBODIMENTS

The stabilized aqueous coenzyme solutions herein can be used in the clinical field for the determination of the following constituents in biological fluids:
1. glutamic-oxalacetic transaminase (SGOT);
2. glutamic-pyruvic transaminase (SGPT);
3. lactic dehydrogenase (LDH);
4. creatine phosphokinase (CPK);
5. α-hydroxybuteric dehydrogenase (α-HBD)
6. glucose (via hexokinase-G-6-PDH or glucose dehydrogenase); and
7. blood urea nitrogen (BUN).
8. triglycerides The stabilized coenzyme solutions are prepared by adding a regenerative enzyme to the aqueous solution containing the coenzyme to be regenerated. In addition to adding the regenerative enzyme, the substrate with which the enzyme exerts catalytic action is also added. The addition of the regenerative enzyme and substrate to the coenzyme solution or assay system provides regeneration of the coenzyme thus, in effect, a stabilization of the coenzyme. To the coenzyme solution or assay system can also be added the coenzyme form such as reduced or oxidized which, upon interaction with the substrate and enzyme, produces the other coenzyme form, oxidized or reduced respectively. For example with the coenzyme NAD or NADH, if it is desired to stabilize NADH, then NAD can be added to the solution along with the appropriate enzyme and substrate for generating NADH. The presence of the coenzyme conversion form aids in the regeneration of the coenzyme as its presence starts to generate the coenzyme as soon as the coenzyme begins to convert or degrade.

As used herein, the term "system" shall include the solution or solutions of reagents including enzymes and coenzymes in appropriate solvents or emulsants needed to perform a clinical assay.

As used herein, the term "stabilized" is used in a broader sense than is implied by the general definition. What Applicant herein means is that the coenzymes are maintained in an acceptable concentration even though particular coenzyme molecules may have been converted or degraded. In addition, the term is used herein to mean that the coenzyme concentration in aqueous solution, prepared as described herein, is maintained at an apparent slower rate of degradation than would be expected for the coenzyme in aqueous solution alone. The terms "degrade, degradation and the like" are used herein in their accepted definitions but include the conversion of a coenzyme to the coenzyme conversion product, e.g., NADH to NAD.

In preparing the stabilized solutions and clinical assay systems herein, an enzyme and substrate are selected that are not present in the clinical assay system and which are not present in the specimen being assayed. In addition, the enzyme and substrate are selected which react with the converted (oxidized or reduced) coenzyme to form the coenzyme desired.

The invention herein and process of making the stabilized solutions is described herein with regard to the stabilization of the coenzyme nicotinamide-adenine dinucleotide, NAD, or its reduced form NADH. With regard to clinical assay of BUN, SGOT, SGPT, LDH and α-HBD the solutions herein provide stabilization of the coenzyme NADH. With regard to clinical assay for CPK and glucose, the solutions herein provide stabilization of the coenzyme NAD.

In a particularly preferred embodiment, the stabilized coenzyme solutions herein are used in the clinical assay of blood-urea-nitrogen (BUN). This preferred stabilized coenzyme solution will be disclosed herein. The preparation of the stabilized coenzyme solutions useful in the other clinical assays will become apparent to one skilled in the art after learning the stabilized coenzyme solution and method of preparing it for the BUN clinical assay.

Urea present in the body can be quantitatively measured by the following reaction sequence:

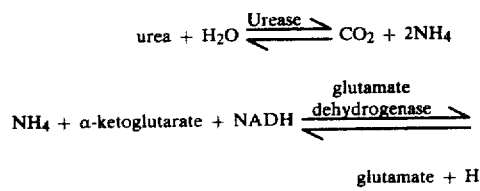

The reaction can be followed quantitatively using photometric methods of analysis. Photometric analysis is possible as the coenzyme NADH exhibits an absorption at 340 nm and NAD does not. The conversion rate of NADH to NAD is a direct function of ammonia concentration which in turn is a function of urea concentration. Thus, by measuring the disappearance rate of NADH in the ultraviolet mode at 340 nm, the BUN can be determined.

The reduced form of nicotinamide-adenine dinucleotide, NADH, is extremely unstable in aqueous solution. However, the present stabilized solutions provide a heretofore unknown stability of the coenzyme NADH in aqueous solution.

To perform a BUN analysis, the clinical assay system requires the presence of: urease; α-ketoglutarate; NADH; and glutamate dehydrogenase. Because of the presence of NADH, such systems are prepared in the absence of water or are prepared in the clinical laboratory as needed.

The stabilized enzymic and coenzymic solutions herein, useful in clinical assay, are provided by supplying an enzymic regeneration of the degraded coenzyme in the clinical assay system. The enzymic production of the coenzyme NADH from the apparent degradation product (and coenzyme) NAD can be performed by the following reaction sequence:

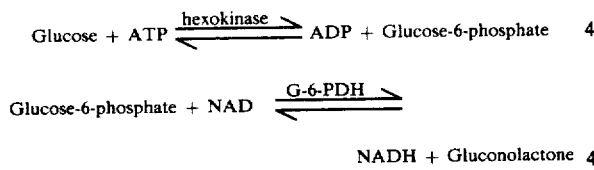

The above reaction sequence produces reduced nicotinamide-adenine dinucleotide and can, therefore, be employed to regenerate NADH in a clinical assay system which utilizes the oxidation of NADH to NAD. In order to utilize the above reaction sequence the substrate, glucose, the enzymes hexokinase and G-6-PDH and the coenzyme ATP are added to the clinical assay system. In addition to adding glucose, ATP, hexokinase, and G-6-PDH to the system, a small amount of NAD, the coenzyme degradation product, can optionally be added. The addition of the coenzyme conversion product, NAD, with which the enzyme, hexokinase and G-6-PDH, and glucose substrate are reactive to form the coenzyme NADH permits the formation of NADH at about the same time that the initial NADH begins to degrade to products other than NAD or convert to NAD.

Two different clinical assay methods are available for determining BUN. The first method is the kinetic or rate measuring method and the second method is the end point method. Two separate stabilized coenzyme systems can be used in the methods. Both systems are described hereinafter with the first system described being for the kinetic or rate measuring method.

The stabilized coenzyme clinical assay system for the determination of BUN is produced by forming two separate reagent solutions: a substrate reagent solution and a coenzyme solution. The two reagent solutions are combined to provide a working solution useful in the clinical assay of BUN.

The substrate reagent solution is prepared by dissolving about 100 IU/l to about 10,000 IU/l urease in a buffer solution of triethanolamine. The buffer solution is about 0.025 to about 1 molar solution of triethanolamine (TEA) in water. The upper limit for the urease concentration is preferably about 10,000 IU/l. Greater amounts can be used if urease is not used as the rate limiting enzyme (or reactant) in the kinetic reaction scheme above. If urease is the rate limiting enzyme at concentrations greater than about 10,000 IU/l, it is difficult to distinguish among concentrations of urea because such higher urease concentrations provide a faster rate of reaction and it is the rate of the reaction that is being measured and quantitatively correlated to the urea concentration. A urease concentration to provide about 100 IU/l is preferred as the lower limit because urease activities below about 100 IU/l, although they can be utilized, provide a sensitivity problem with regard to determining urea concentration as the rate of the reaction is slowed.

The buffer solution is preferably a 0.3 molar solution of triethanolamine in water. If the buffer solution is greater than one molar, the triethanolamine can inhibit the enzyme reaction because of salt inhibition. In addition, if the triethanolamine is present in a concentration of about 0.025 to about 1 molar, there is some stabilizing of the enzymes present.

To the urease buffered solution is added α-ketoglutarate (α-Kg). Preferably, the α-ketoglutarate is added in an amount of about 0.1 to about 5 g/l of solution and more preferably about 1.4 g/l. Amounts greater than 5 g/l can be used but are not preferred because α-ketoglutarate absorbs ultraviolet light within the same range as NADH. In addition, a greater amount can tend to reduce the rate of the measured reaction. Amounts less than 0.1 g/l can be used but are not preferred because lower amounts do not provide an instantaneous reaction between the ammonia, NADH and α-ketoglutarate. That is, lower amounts of α-ketoglutarate produce a lower reaction rate.

The enzyme glutamate dehydrogenase (GLDH) is then added to the solution. The GLDH enzyme is added in an amount of about twice (up to 100 times) the activity of the urease up to about 60,000 IU/l. Preferably, the GLDH is in an amount of about 15,000 to about 30,000 IU/l. Greater amounts than 60,000 IU/l can be used but no significant benefit is achieved and greater amounts are more expensive. The selection of the upper limit, therefore, is based upon economics and generally 60,000 IU/l can be used economically. The lower limit is selected so as to convert the ammonia formed from the urea by the primary reaction as quickly as it is formed so that the first reaction is the overall rate determining reaction for the two reaction sequence.

To the resultant solution is then added adenosine-5' diphosphate (ADP). The ADP is added because it activates and stabilizes GLDH. The presence of ADP has an effect that about doubles the activity of GLDH. ADP can be added in any amount. It is added in an amount greater than 0.1 g/l in order to provide such GLDH activity doubling ability. Essentially, there is no upper limit in the amount of ADP which can be added, but for practical considerations, it is preferred that about 20 g/l is the greatest amount of ADP to be added. Preferably, about 2.5 g/l of ADP is added.

A polyhydroxy organic compound containing from 2 to 4 hydroxyl groups and 2 to 10 carbon atoms is added to the solution. Preferably, the polyhydroxy organic compound is selected from the group consisting of glycerol, ethylene glycol, sorbitol, mannitol and propylene glycol. Most preferred is glycerol.

The polyhydroxy organic compound is added in an amount from about 5 to about 40 percent by volume of the substrate solution. Amounts greater than 40 percent by volume can be used but increase the viscosity of the solution. A high viscosity inhibits enzyme activity and the use of the solution in clinical assays. Amounts less than 5 percent by volume can be used but it is preferred to use at least 5 percent by volume as the polyhydroxy organic compound exhibits a stabilizing effect upon the enzymes and coenzymes in the solution. Preferably, glycerol in an amount of about 15 percent by volume is added to the above described preparation of the substrate solution for BUN analysis.

The substrate solution, as prepared above, can be used in the clinical assay of BUN when combined with the following described coenzyme solution. The combined solutions, however, have a limited effective coenzyme life because of degradation of the coenzyme NADH. The effective and useful life of the combined reagent can be increased by adding an enzyme and substrate system for regenerating the coenzyme from the coenzyme conversion product. For the BUN clinical assay the conversion product of NADH can be the oxidized form of nicotinamide-adenine dinucleotide or NAD. Other degradation products of NADH can be formed as NADH can degrade at some molecular sites that do not yield NAD.

To regenerate NADH from NAD, the enzyme and substrate system added to the above-prepared substrate solution is ATP, glucose, hexokinose and G-6-PDH. ATP is added in an amount from about 10 mg/l to about 10 g/l. Preferably, about 1 g/l of ATP is added. Glucose is added in an amount from about 10 mg/l to about 10 g/l and preferably about 1 g/l. The enzyme hexokinase is added in an amount from about 1 IU/l to about 50 IU/l. For the above described substrate solution it is preferred to add about 20 IU/l of hexokinase. The enzyme G-6-PDH is added to the substrate solution in an amount that is about one to about ten times the activity of the hexokinase activity. Preferably about three times the hexokinase activity. For the above-described substrate solution, it is preferred to add about 60 IU/l of G-6-PDH. The substrate solution prepared in this manner with these constituents provides a greater stability for the combined working solution for use in clinical assay.

The coenzyme reagent solution is prepared by dissolving the coenzyme NADH in water-free propylene glycol (1,2-propanediol). Essentially water-free propylene glycol is used in the preparation of the coenzyme reagent solution because NADH degrades in the presence of water. Thus, to increase the shelf life of the coenzyme solution it is prepared in a water-free solution. A water absorbing agent such as an inert hygroscopic agent as is described in U.S. Pat. No. 4,153,511, the entire disclosure of which is incorporated herein by this reference, can be used to maintain the absence of water. A small amount of organic salt of NAD can also be incorporated in this coenzyme solution, such as the tris(hydroxymethyl)aminomethane salt of NAD (NAD tris salt).

The coenzyme reagent solution is prepared such that the concentration of NADH is about 10 mM. There is essentially no limits to the amount of NADH that is needed other than absorbance. That is, an amount is required that provides a measurable absorbance but which is not too great an absorbance as to require dilution of the assay solution placed in the spectrophotometer. The NADH can be present up to its solubility limit and is preferably as concentrated as possible since propylene glycol is a relatively strong enzyme inhibitor and can interfere with the primary enzyme activity in the clinical assay system if too great an amount is carried into the assay from the coenzyme reagent solution.

To perform a clinical assay for BUN, the substrate reagent solution and coenzyme reagent solution are combined to form a combined working reagent solution. Such a combined working reagent solution has a stability of about 6 months at 4° C. which was heretofore unexpected because of the presence of water and NADH. Without adding the enzyme and substrate system for regenerating NADH from NAD, the working solution formed by combining the substrate reagent solution and coenzyme solution has a stability of about 24 to 72 hours at 4° C. The coenzyme reagent solution and substrate reagent solution are combined in a ratio of about 1 part coenzyme reagent to about 40 parts substrate solution.

The end point method of clinical analysis of BUN is also conducted beginning with two solutions, a substrate reagent solution and a coenzyme reagent solution. Two solutions are necessitated because of the aqueous degradation of NADH. Prior to performing the clinical assay, the two solutions are combined to form a working reagent solution.

The substrate reagent solution for the end point method is prepared in the same manner as the substrate reagent solution for the above rate measuring method of assay. However, the preferred substrate reagent solution is prepared with the following concentrations:

| Urease | 20,000 IU/l |
| --- | --- |
| GLDH | 18,000 IU/l |
| ADP | 0.6 g/l |
| α-KG | 1.25 g/l |
| TEA | 0.3 M |
| Glycerol | 15% v/v |
| NaN$_3$ | 0.1% by wt. |
| ATP | 0.3 g/l |
| Glucose | 1.0 g/l |
| Hexokinase | 2 IU/l–500 IU/l |
| G-6-PDH | 6 IU/l–1500 IU/l |

The coenzyme reagent solution is prepared as above.

The concentrations of the components are different between the two preferred embodiments because it is desirable to have the BUN assay by the end point method proceed at a faster rate in order to reach the end point quicker. With regard to the amounts of ATP, glucose, hexokinase and G-6-PDH it is important in the end point method to not exceed the rate of NADH degradation in the overall solution, which degradation is not brought about by the presence of urea through the primary reaction. That is, it is important not to exceed the rate of NADH degradation in a blank specimen. To limit the rate production of NADH from NAD the glucose and/or ATP concentration can be adjusted. The enzyme amounts are the easiest to adjust, however, leaving glucose and ATP in excess. It was found that the above concentrations provided close matching of the rate of NADH degradation in a blank with the rate of NADH enzymic production from NAD using the above enzymes and substrates, and is most resistant to elevated temperatures.

In the end point method, the substrate reagent solution and coenzyme reagent solution are combined in a ratio of about 40:1 respectively. Using either method of assay to determine BUN the combined concentrate solution is mixed with the sample to be assayed. Preferably, about 5 to 10 μl of the sample are added to about 1 ml of the combined concentrate solution and then either the rate of reaction or end point are determined such as by photometric analysis.

A second substrate reagent solution which can be prepared for use in BUN analysis can be prepared as above with the exception that a different enzyme and substrate system for the regeneration of NADH is added in the place of ATP, glucose, hexokinase and G-6-PDH. To prepare the substrate reagent solutions the above procedure is followed except for the addition of ATP, glucose, hexokinase and G-6-PDH. The enzyme and substrate system that is added to the substrate solution comprises glucose dehydrogenase and glucose. By adding glucose dehydrogenase and glucose, the NADH that degrades to form NAD can be regenerated to NADH. Glucose dehydrogenase is acceptable for regenerating NADH as it is not present in the BUN assay system nor in human serum. Since glucose is added in excess to the assay system, serum glucose will have no observable effect on the reaction.

It is to be realized that only preferred embodiments of the invention have been described and that numerous substitutions, modifications and alterations are permissible without departing from the spirit and scope of the invention. Other coenzymes, other than NADH, can be regenerated enzymically from their degradation product. To enzymically regenerate such coenzymes there is added an enzyme or enzymes and complementary substrate with which the enzyme can react along with the degradation product of the coenzyme to regenerate the coenzyme.

For example, an enzyme regeneration system can be used to regenerate NAD that degrades to its reduced form NADH in some clinical assays such as assays for creatine phosphokinase (CPK) and glucose. To regenerate NAD, a suitable amount of α-ketoglutarate, GLDH and ammonia can be added to the assay system.

EXAMPLE I

Reagents useful for the clinical assay of BUN by the rate measuring method were prepared. The two reagent solutions prepared provided, upon combination, a stabilized aqueous coenzyme solution which can be used in the assay of BUN by photometric methods of analysis. The two reagents had the following compositions:

| Substrate Reagent Solution | |
|---|---|
| Urease | 4000 IU/l |
| α-ketoglutarate | 0.4 g/l |
| GLDH | 18,000 IU/l |
| ADP | 2.5 g/l |
| Buffer (Triethanolamine) | 40.5 ml/l |
| Glycerol | 15% v/v |
| ATP | 100 mg |

| -continued | |
|---|---|
| Glucose | 100 mg |
| Hexokinase | 20 IU/l |
| G-6-PDH | 60 IU/l |
| Coenzyme Reagent Solution | |
| NADH | 10 mM |
| 1,2-propanediol (H$_2$O free) | to make |

The substrate reagent solution exhibited a predicted stability of 18 months at 4° C. with a loss of less than about 20 percent of the enzyme activity.

The coenzyme reagent solution had a predicted stability of about four years at about 4° C. when maintained closed and water free.

The two solutions are combined in a ratio of 1 part coenzyme reagent solution to 40 parts substrate reagent solution prior to performing BUN assay. The concentration of the various components remains essentially the same with the exception of NADH which becomes about 0.25 mM. The combined solution has a stability of about 6 months at 4° C. This stability is greater than the stability of a combined solution prepared by combining a coenzyme reagent solution and substrate reagent solution prepared as above with the exception that no ATP, glucose, hexokinase and G-6-PDH are present. Such a combined solution exhibited only a 24 to 72 hour stability at 4° C.

EXAMPLE II

A substrate reagent solution and coenzyme reagent solution were prepared as described in Example I with the exception that the substrate reagent solution had the following composition:

| Substrate Reagent Solution | |
|---|---|
| Urease | 400 IU/l |
| α-ketogluterate | 1.4 g/l |
| GLDH | 30,000 IU/l |
| ADP | 2.5 g/l |
| Buffer (Triethanolamine) | 40.5 ml/l |
| Glycerol | 15% v/v |
| ATP | 30 mg/dl |
| Glucose | 100 mg/dl |
| Hexokinase | 4 IU/l |
| G-6-PDH | 12 IU/l |

The substrate reagent solution exhibits a predicted stability of 18 months at 4° C. with a loss of less than about 20 percent of the enzyme activity.

The two solutions (coenzyme and substrate) are combined in a ratio of 1 part coenzyme reagent solution to 40 parts substrate reagent solution prior to performing BUN assay. The combined solution has a stability of about 4 months at 4° C.

EXAMPLE III

Reagents useful for the clinical assay of BUN by the end point determining method were prepared. A two-reagent system was prepared wherein the two reagents had the following compositions:

| Substrate Reagent Solution | |
|---|---|
| Urease | 20,000 IU/l |
| GLDH | 18,000 IU/l |
| ADP | 0.6 g/l |
| α-ketoglutarate | 1.25 g/l |
| Buffer (TEA) | 0.3 M |
| Glycerol | 15% v/v |

| -continued | |
|---|---|
| NaN₃ | 0.1% w/v |
| ATP | 0.3 g/l |
| Glucose | 1.0 g/l |
| Hexokinase | 2 IU/l |
| G-6-PDH | 6 IU/l |
| Coenzyme Reagent Solution | |
| NADH | 10 mM |
| 1,2-propanediol | to make |

The two reagent solutions are combined in a ratio of one part coenzyme reagent solution and 40 parts substrate reagent solution. The combined coenzyme solution has a stability of about 3 months at 4° C.

EXAMPLE IV

Two reagents are prepared as described in Example I with the exception that a different enzyme and substrate system for regenerating NADH is added. The compositions of the solutions are as follows:

| Substrate Reagent Solution | |
|---|---|
| Urease | 4000 IU/l |
| α-ketoglutarate | 0.4 g/l |
| ADP | 2.5 g/l |
| GLDH | 18,000 IU/l |
| Buffer (TEA) | 40.5 ml/l |
| Glycerol | 15% v/v |
| Glucose dehydrogenase | 20 IU/l |
| Glucose | 100 mg/dl |
| Coenzyme Reagent Solution | |
| NAD tris salt | 200 mg/dl |
| NADH | 10 mM |
| 1,2-propanediol | to make |

When the two reagents are combined in a ratio of 1 part coenzyme reagent solution to 40 parts substrate reagent solution, the combined coenzyme solution has a stability of about 3 months at 4° C.

EXAMPLE V

Reagents useful for the clinical assay of SGOT (AST) activity were prepared. The reagents were based on the following method of determining AST activity in serum:

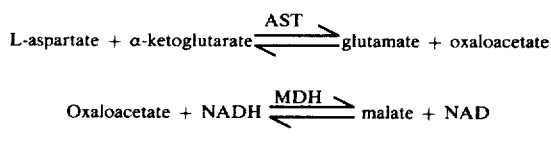

by providing the reactants L-aspartate and α-ketoglutarate in excess in the primary reaction, and providing the coupling enzyme MDH and coenzyme NADH also in excess, the rate limiting AST enzyme activity is established.

Stabilization of the enzymes MDH and LDH in aqueous media are treated in co-pending U.S. patent application Ser. No. 898,704 of Modrovich, entitled STABILIZED LIQUID ENZYME REAGENT COMPOSITIONS, filed Apr. 24, 1978, now U.S. Pat. No. 4,310,625. Stabilization of the coenzymes NADH or NADPH is disclosed in issued U.S. Pat. No. 4,153,511 and co-pending U.S. patent application Ser. No. 775,833 of Modrovich, entitled STABILIZED LIQUID COENZYME COMPOSITIONS, filed Mar. 9, 1977, now U.S. Pat. No. 4,310,624 well as co-pending U.S. patent application Ser. No. 722,565 of Modrovich, entitled STABILIZED LIQUID ENZYME AND COENZYME COMPOSITIONS AND METHOD OF PREPARING SAME, filed Sept. 13, 1976, now abandoned. The entire disclosures of these references are incorporated herein by this reference.

Based on the teachings disclosed in the above cited references, one embodiment of a stable liquid enzyme reagent useful for AST determination is as follows:

| Substrate Reagent: pH 7.8 ± 0.2 | |
|---|---|
| L-aspartic Acid | 200 mM |
| Tris(hydroxymethyl) aminomethane | 75 mM |
| Gelatin | 0.1% w/v |
| Sodium Azide | 0.1% w/v |
| Glycerol | 3.7% v/v |
| MDH | ≧2000 IU/l |
| LDH | ≧2000 IU/l |
| α-ketoglutarate | 16 mM |
| Glucose | 0.1% w/v |
| Glucose dehydrogenase | 5 IU/l–100 IU/l |
| Hydrochloric acid | To adjust pH |
| Sodium hydroxide | To adjust pH |
| Coenzyme Reagent | |
| NADH | 5.9 mM |
| NAD | 200 mg/dl |
| 1,2-propanediol (H₂O free) | to make |
| Inert desiccant | as needed |

The substrate solution is stable one year under refrigertion, the coenzyme solution is stable about four years under refrigeration.

The two solutions are combined in a ratio of one part coenzyme reagent solution to 35 parts substrate reagent solution prior to AST assay. The concentration of the various components remains essentially the same with the exception of NADH and NAD which becomes about 0.17 mM and 5.7 mg/dl respectively. The combined solution has a stability of about 30 days at 4° C. Omitting glucose dehydrogenase, glucose and NAD yielded a combined solution having a stability of only 48 hours at 4° C.

EXAMPLE VI

The procedure of Example V is repeated in every essential detail to prepare a substrate reagent solution and coenzyme reagent solution with the exception that the substrate reagent solution has the following compositions:

| Substrate Reagent Solution: pH 7.8 ± 0.2 | |
|---|---|
| L-aspartic Acid | 200 mM |
| Tris (hydroxymethyl)aminomethane | 75 mM |
| Gelatin | 0.1% w/v |
| Sodium Azide | 0.1% w/v |
| Glycerol | 3.7% v/v |
| MDH | ≧2000 IU/l |
| LDH | ≧2000 IU/l |
| α-ketoglutarate | 16 mM |
| Glucose | 0.1% w/v |
| Hexokinase | 3 IU/l |
| G-6-PDH | 10 IU/l |
| Hydrochloric Acid | To adjust pH |
| Sodium Hydroxide | To adjust pH | and the coenzyme reagent solution has the following compositions:

| Coenzyme Reagent Solution | |
|---|---|
| NADH | 5.9 mM |
| ATP | 500 mg/dl |

| Coenzyme Reagent Solution | |
|---|---|
| 1,2-propanediol (H₂O free) | to make |
| Inert desiccant | as needed |

The two reagent solutions are combined as described in Example V. The combined solution exhibits a stability of about 30 days at 4° C.

EXAMPLE VII

Reagents useful for the clinical assay of SGPT (ALT) were prepared based on the following ALT determining reaction sequence:

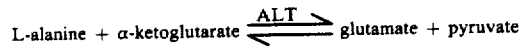

L-alanine + α-ketoglutarate $\xrightleftharpoons{ALT}$ glutamate + pyruvate

Pyruvate + NADH $\xrightleftharpoons{LDH}$ lactate + NAD

One embodiment of a stable liquid reagent composition follows:

| Substrate Reagent: pH 7.8 ± 0.2 | |
|---|---|
| L-alanine | 276 mM |
| α-ketoglutarate | 16 MM |
| LDH | ≧2000 IU/l |
| Tris(hydroxymethyl)aminomethane | 75 mM |
| Gelatin | 0.1% w/v |
| Sodium azide | 0.1% w/v |
| Glycerol | 4% v/v |
| Glucose | 0.1% w/v |
| Glucose dehydrogenase | 1.5 IU/l–50 IU/l |
| Hydrochloric acid | to adjust pH |
| Sodium hydroxide | to adjust pH |
| Coenzyme Reagent | |
| NADH | 5.9 mM |
| NAD | 200 mg/dl |
| 1,2-propanediol | to make |
| Inert desiccant | as needed |

The substrate reagent solution is stable about 18 months at 4° C. The coenzyme reagent solution is stable about 4 years at 4° C. The two solutions are combined in a ratio of 1 part coenzyme solution to 35 parts substrate solution prior to assay. The combined solution has a stability of about 30 days at 4° C.

Omitting glucose dehydrogenase, glucose and NAD yielded a combined solution stability of only 48 hours at 4° C.

EXAMPLE VIII

The procedure of Example VII is repeated in every essential detail with the exception that the substrate reagent solution has the following compositions:

| Substrate Reagent Solution: pH 7.8 ± 0.2 | |
|---|---|
| L-alanine | 276 mM |
| α-ketoglutarate | 16 mM |
| LDH | ≧2000 IU/l |
| Tris(hydroxymethal)aminomethane | 75 mM |
| Gelatin | 0.1% w/v |
| Sodium Azide | 0.1% w/v |
| Glycerol | 4% v/v |
| Glucose | 0.1% w/v |
| Hexokinase | 2 IU/l |
| G-6-PDH | 6 IU/l |
| HCl and/or NaOH | to adjust pH | and the coenzyme reagent solution has the following composition:

| Coenzyme Reagent Solution | |
|---|---|
| NADH | 5.9 mM |
| ATP | 250 mg/dl |
| 1,2-propanediol (H₂O free) | to make |
| Inert desiccant | as needed |

The two solutions were combined as in Example VII. The combined solution exhibits a stability of about 30 days at 4° C.

EXAMPLE IX

Reagents useful for the clinical assay of CPK (CK) activity were prepared, based on the following CK determining reaction sequence:

Creatine phosphate + ADP $\xrightleftharpoons{CK}$ Creatine + ATP

ATP + glucose $\xrightleftharpoons{HK}$ glucose-6-phosphate + ADP

Glucose-6-phosphate + NAD $\xrightleftharpoons{G-6-PDH}$ gluconolactone + NADH

Stabilization of the labile ingredients in liquid media of AMP, ADP, creatine phosphate, HK, G-6-PDH, NAD are disclosed in co-pending U.S. patent application Ser. No. 722,565. One embodiment of a stable liquid enzyme reagent system useful for CK determination is:

| Substrate Reagent: pH 8.2 ± 0.4 | |
|---|---|
| Creatine phosphate | 300 mM |
| ADP | 28 mM |
| AMP | 25 mM |
| G-6-PDH | ≧40,000 IU/l |
| Glycerol | 30% v/v |
| Sodium azide | 0.1% w/v |
| Phosphate tris buffer | 100 mM |
| Glutamate dehydrogenase | 48 IU/l |
| α-ketoglutarate | 1.2 mM |
| Coenzyme Reagent: pH 6.0 ± 0.5 | |
| NAD | 30 mM |
| AMP, free acid | 22 mM |
| Hexokinase | ≧160,000 IU/l |
| Magnesium acetate | 200 mM |
| Glycerol | 50% v/v |
| Tris(hydroxymethyl)aminomethane | to adjust pH |
| Buffer Reagent Solution: pH 5.3 ± 0.5 | |
| Glucose | 83 mM |
| N—acetyl cysteine | 12 mM |
| Dithiothreitol | 65 mM |
| Imidazole | 25 mM |
| Ammonium sulfate | 0.2 mM |

The above solutions are stable at 4° C. for about two years. The solutions are combined in a ratio of 1 part substrate solution, 1 part coenzyme solution and 10 parts buffer solution prior to CK assay. The concentration of the various components in the combined reagent reflects dilution effects due to combining. The combined solution has a stability of about 30 days at 4° C.

Omitting ammonium sulfate, α-ketoglutarate and glutamate dehydrogenase yielded a combined solution stability of 5 days at 4° C.

It is apparent from the examples above that maintaining coenzyme levels of NADH/NAD is the critical point addressed in this disclosure. It is important to recognize, however, that this is critical only within wide tolerance levels. For example, an NADH level of 0.1 mM in either AST or ALT working reagent is quite sufficient where the upper limit of tolerance is determined by practical considerations such as absorbance of the working (combined) reagent at 340 nm, which is an instrumental limitation, as most commercially available spectrophotometers are inaccurate above 2.000 units of absorbance equivalent to about 0.3 mM NADH concentration. Within this limit NADH can vary without any significant effect on assay results.

Similarly, the greatest limitation of CK working (combined) reagent stability is the absorbance increase due to NADH accumulation in the reagent caused by reduction of NAD to NADH by enzymic impurities and sulfhydryl activators of CK present in the solution, i.e., dithiothreitol, N-acetyl cysteine. This accumulation raises the working reagent absorbance from a starting level of about 0.200 to about 1.0 in 5 days at 4° C. Since this is an assay monitored by increasing rate of absorbance (i.e., NADH generation) a high initial absorbance severely limits the assay's dynamic range. Continuous oxidation of NADH to NAD via the GLDH route, for example, keeps initial absorbance at acceptable levels for 30 days at 4° C. without significant degradation in other reactive components.

What is claimed is:

1. A stabilized aqueous coenzyme solution for use in the clinical assay of a selected biological constituent through the enzymic reaction of an enzyme or enzymes with selective substrates for the enzymes and a labile coenzyme, said aqueous coenzyme solution comprising:
    (a) at least one first enzyme and a first substrate for selectively reacting with the first enzyme in the assay of the selected biological constituent;
    (b) a labile coenzyme for interacting with the first enzyme and first substrate, which labile coenzyme degrades in said aqueous solution to a coenzyme conversion product; and
    (c) an enzyme and substrate system comprising at least one second enzyme and a selective second substrate for the second enzyme, which second enzyme and second substrate react in said aqueous enzyme solution with the coenzyme conversion product to form the coenzyme.

2. A stabilized aqueous coenzyme solution for use in a clinical assay of a biological constituent selected from the group consisting of:
    glutamic-oxalacetic transaminase (SGOT);
    glutamic-pyruvic transaminase (SGPT);
    lactic dehydrogenase (LDH);
    creatine phosphokinase (CPK);
    α-hydroxybuteric dehydrogenase (α-HBD);
    glucose (via hexokinase-G-6-PDH);
    glucose (via glucose dehydrogenase);
    blood urea nitrogen (BUN); and
    triglycerides
through the reaction of an enzyme or enzymes with a selective substrate for the enzymes, and a coenzyme, said aqueous coenzyme solution comprising:
    (a) at least one first enzyme and a first substrate for selectively interacting with the first enzyme in the assay for the selected biological constituent;
    (b) a labile coenzyme for interacting with the first enzyme and substrate in the assay to form a coenzyme conversion product and which labile coenzyme degrades in said aqueous solution to said coenzyme reaction product; and
    (c) an enzyme and substrate system comprising at least one second enzyme and a selective second substrate for the second enzyme which react in said aqueous coenzyme solution with the coenzyme conversion product of degradation to regenerate the coenzyme.

3. A stabilized aqueous coenzyme solution as recited in claim 1 or 2 wherein the enzyme and substrate system comprises at least one second enzyme and selective second substrate different from the first enzyme and first substrate present in the solution for the assay of the selected biological constituent.

4. A stabilized aqueous coenzyme solution as recited in claim 1 or 2 wherein the coenzyme is selected from the group consisting of NADH and NAD.

5. A stabilized aqueous coenzyme solution as recited in claim 1 or 2 wherein the selected biological constituent assayed is selected from the group consisting of SGOT, SGPT, LDH, α-HBD and BUN and wherein the coenzyme is NADH.

6. A stabilized aqueous coenzyme solution as recited in claim 5 wherein the enzyme and substrate system comprises ATP, glucose, hexokinase and G-6-PDH.

7. A stabilized aqueous coenzyme solution as recited in claim 5 wherein the enzyme and substrate system comprises glucose dehydrogenase and glucose.

8. A stabilized aqueous coenzyme solution as recited in claim 1 or 2 wherein the selected biological constituent assayed is selected from the group consisting of CPK, glucose (via hexokinase-G-6-PDH) and glucose (via glucose dehydrogenase).

9. A stabilized aqueous coenzyme solution as recited in claim 8 wherein the enzyme and substrate system comprises ammonium sulfate, α-ketoglutarate and glutamate dehydrogenase.

10. A stabilized aqueous coenzyme solution as recited in claim 1, 2, 6, 7 or 9 wherein the enzyme and substrate system further comprises coenzyme conversion product.

11. A stabilized coenzyme solution as claimed in claim 1 or 2 in which at least one polyhydroxy organic compound is present.

12. A stabilized coenzyme solution as claimed in claim 10 in which a polyhydroxy organic compound is present.

13. A stabilized aqueous coenzyme solution for use in the biological assay of BUN, the aqueous coenzyme solution comprising urease, α-ketoglutarate, GLDH, ADP, glycerol, NADH, ATP, glucose, hexokinase, and G-6-PDH dissolved in an aqueous solution of triethanolamine.

14. A stabilized aqueous coenzyme solution for use in the biological assay of BUN, the aqueous coenzyme solution comprising from about 100 to about 10,000 IU/l urease; from about 0.1 to about 5 g/l α-ketoglutarate; from about twice the urease activity to about 60,000 IU/l GLDH; about 0.1 to about 20 g/l ADP; about 5 to about 40 percent by volume glycerol; at least about 0.25 mM of NADH; about 10 mg/l to about 10 g/l ATP; about 10 mg/l to about 10 g/l glucose; about 1 IU/l to about 50 IU/l hexokinase; and G-6-PDH in an amount providing an activity about one to about ten times the activity of the hexokinase dissolved in about a 0.025 to about 1 molar aqueous solution of triethanolamine.

15. A stabilized aqueous coenzyme solution for use in the biological assay of SGOT, the aqueous coenzyme solution comprising L-aspartic acid; tris(hydroxymethyl)aminomethane; gelatin; sodium azide; glycerol; MDH; LDH; α-ketoglutarate, glucose; glucose dehydrogenase; NADH; NAD; and 1,2-propanediol in an aqueous solution having a pH of about 7.8±0.2 provided by a buffering agent selected from HCl, NaOH and mixture thereof.

16. A stabilized aqueous coenzyme solution for use in the biological assay of SGOT, the aqueous coenzyme solution comprising L-aspartic acid; tris(hydroxymethyl)aminomethane; gelatin, sodium azide; glycerol; MDH; LDH; α-ketoglutarate; glucose; hexokinase; G-6-PDH; NADH; ATP and 1,2-propanediol in an aqueous solution having a pH of about 7.8±0.2 provided by a buffering agent selected from HCl, and NaOH and mixture thereof.

17. A stabilized aqueous coenzyme solution for use in the biological assay of SGPT, the aqueous coenzyme solution comprising L-alanine; α-ketoglutarate; LDH; tris(hydroxymethyl) aminomethane; gelatin; sodium azide; glycerol; glucose; glucose dehydrogenase; NADH; NAD and 1,2-propanediol in an aqueous solution having a pH of about 7.8±0.2 provided by a buffering agent selected from HCl, NaOH and mixture thereof.

18. A stabilized aqueous coenzyme solution for use in the biological assay of SGPT, the aqueous coenzyme solution comprising L-alanine; α-ketoglutarate; LDH; tris(hydroxymethyl)aminomethane; gelatin, sodium azide; glycerol; glucose; hexokinase; G-6-PDH; NADH; ATP and 1,2-propanediol in an aqueous solution having a pH of about 7.8±0.2 provided by a buffering agent selected from HCl, NaOH and mixture thereof.

19. A stabilized aqueous coenzyme solution for use in the biological assay of CPK, the aqueous coenzyme solution comprising creatine phosphate; ADP; AMP; G-6-PDH; glycerol; sodium azide; phosphate tris buffer; glutamate dehydrogenase; NAD; AMP; hexokinase; magnesium acetate; tris(hydroxymethyl)aminomethane; glucose; N-acetyl cysteine; dithiothreitol; imidazole; and ammonium sulfate.

20. A method of stabilizing a labile coenzyme in an aqueous clinical assay solution comprising at least one first enzyme, selective first substrate for reacting with the first enzyme and a labile coenzyme for reacting with the first enzyme and first substrate in a diagnostic assay of a selected biological constituent, said coenzyme degrading in aqueous solution to produce a coenzyme conversion product, the method comprising adding to the clinical assay solution an enzyme and substrate system comprising at least one second enzyme and second substrate which selectively react with the coenzyme conversion product to produce the coenzyme.

21. A method as recited in claim 20 further comprising adding to the clinical assay solution coenzyme conversion product.

22. A method of stabilizing a labile coenzyme for use in an aqueous clinical assay of a selected biological constituent, which coenzyme degrades to a coenzyme conversion product, the method comprising the steps of:

forming an aqueous substrate solution comprising at least one first enzyme and first substrate for selectively reacting with said first enzyme in the assay of the selected biological constituent and an enzyme and substrate system comprising at least one second enzyme and second substrate capable of reacting with the coenzyme conversion product for regenerating the coenzyme;

forming a coenzyme solution comprising a nonaqueous solution of the labile coenzyme useful in the clinical assay; and combining the substrate solution and coenzyme solution forming a stabilized coenzyme solution for use in an aqueous clinical assay of a selected biological constituent.

23. A method of stabilizing the labile coenzyme NAD in an aqueous clinical assay solution comprising at least one first enzyme, selective first substrate for reacting with the first enzyme and a labile coenzyme for reacting with the first enzyme and first substrate in a diagnostic assay of a selected biological constituent, said coenzyme degrading in aqueous solution to produce a coenzyme conversion product, the method comprising providing to the clinical assay solution in which the labile coenzyme is NAD an enzyme and substrate system comprising at least one second enzyme and second substrate which selectively react with the coenzyme conversion product to form NAD, said provided enzyme and substrate system comprising ammonium sulfate, α-ketoglutarate and dehydrogenase.

24. A method as recited in claim 23 further comprising adding to the clinical assay solution coenzyme conversion product.

25. A method of stabilizing the labile coenzyme NADH in an aqueous clinical assay solution comprising at least one first enzyme, selective first substrate for reacting with the first enzyme and a labile coenzyme for reacting with the first enzyme and first substrate in a diagnostic assay of a selected biological constituent, said coenzyme degrading in aqueous solution to produce a coenzyme conversion product, the method comprising providing in the clinical assay solution in which the labile coenzyme is NADH an enzyme and substrate system comprising at least one second enzyme and second substrate which selectively react with the coenzyme conversion product to form NADH, said provided enzyme and substrate system being selected from the system comprising ATP, glucose, hexokinase and G-6-PDH and the system comprising glucose dehydrogenase and glucose.

26. A method as recited in claim 25 further comprising adding to the clinical assay solution coenzyme conversion product.

27. A method as claimed in claim 23 or 25 in which the formed aqueous clinical assay solution contains a polyhydroxy organic compound.

* * * * *